(12) United States Patent
Gramnäs

(10) Patent No.: US 6,302,918 B1
(45) Date of Patent: Oct. 16, 2001

(54) SHOCK-AND TORQUE ABSORBER IN A LEG PROTHESIS

(75) Inventor: Finn Gramnäs, Hästskovägen 5 (SE)

(73) Assignee: Gramtec Innovation AB, Kinna (SE)

( * ) Notice: Subject to any disclaimer, the term of this patent is extended or adjusted under 35 U.S.C. 154(b) by 0 days.

(21) Appl. No.: 09/424,827

(22) PCT Filed: May 28, 1998

(86) PCT No.: PCT/SE98/01015

§ 371 Date: Nov. 29, 1999

§ 102(e) Date: Nov. 29, 1999

(87) PCT Pub. No.: WO98/56320

PCT Pub. Date: Dec. 17, 1998

(30) Foreign Application Priority Data

May 30, 1977 (SE) .................................................. 9702077

(51) Int. Cl.[7] .............................................. A61F 2/74
(52) U.S. Cl. ............................................. 623/27; 623/52
(58) Field of Search ................................ 623/35, 27, 47, 623/50, 52

(56) References Cited

U.S. PATENT DOCUMENTS

| 3,842,443 | * | 10/1974 | Weber | 3/2 |
| 3,906,552 | * | 9/1975 | Weber | 623/52 |
| 4,038,705 | * | 8/1977 | Owens et al. | 3/2 |
| 4,134,159 | * | 1/1979 | Wilson | 3/2 |
| 4,186,449 | * | 2/1980 | Horvath | 3/2 |
| 4,883,493 | * | 11/1989 | Martel et al. | 623/38 |
| 5,383,939 | * | 1/1995 | James | 623/24 |
| 5,571,205 | * | 11/1996 | James | 623/24 |
| 5,800,562 | * | 9/1998 | Wilkinson | 623/27 |

FOREIGN PATENT DOCUMENTS

| 0413 450 A1 | * | 2/1991 | (EP) | A61F/2/60 |
| 2305363B | | 4/1997 | (GB) | A61F/2/60 |
| WO 95/30391 | | 11/1995 | (WO) | A61F/2/64 |
| WO 98/29059 | | 7/1998 | (WO) | A61F/2/60 |

* cited by examiner

Primary Examiner—Bruce Snow
(74) Attorney, Agent, or Firm—Gardner, Carton & Douglas

(57) ABSTRACT

A device in a leg prosthesis provided with a shock- and torque absorber intended to absorb shocks as well as rotational movements which occur when the foot hits the ground during walking, running, jumping etc. and comprising two parts (10, 11) which are telescopically displaceable and rotatable with sect to each other. Mhm device further comprises a first resilient member (12) arranged between the two telescopic pars (10, 11) and said resilient member is arranged to be compressed at a telescopic movement of said parts in a retracting direction, that a second resilient member (19) is attached to the outer telescopic part (10) and limitedly displaceable in the inner telescopic part (11) limiting the telescopic movement as well as the rotational movement thereof in the outer telescopic part (10).

10 Claims, 5 Drawing Sheets

FIG. 1
FIG. 2
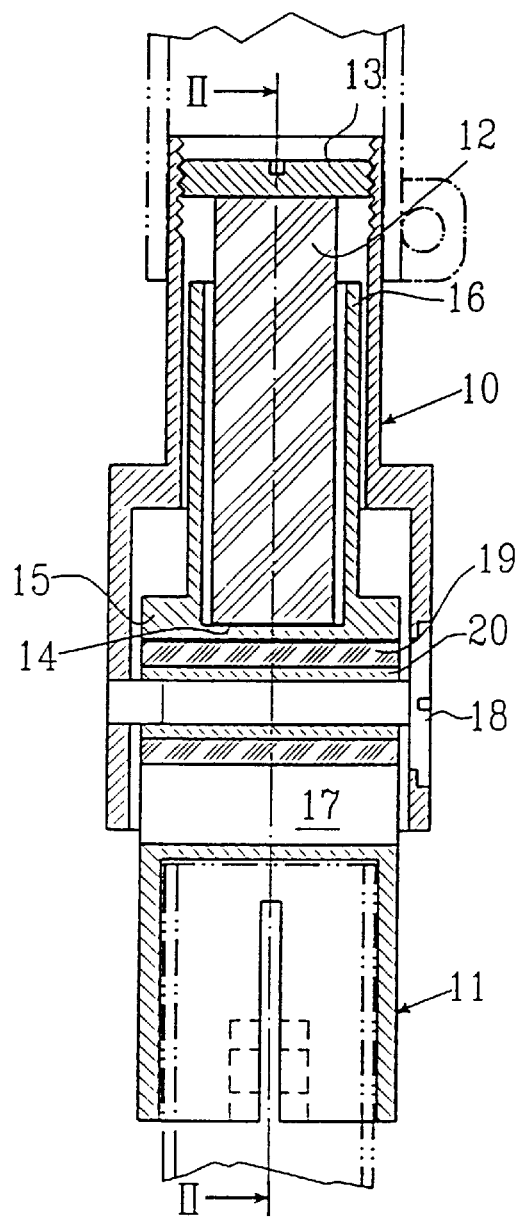
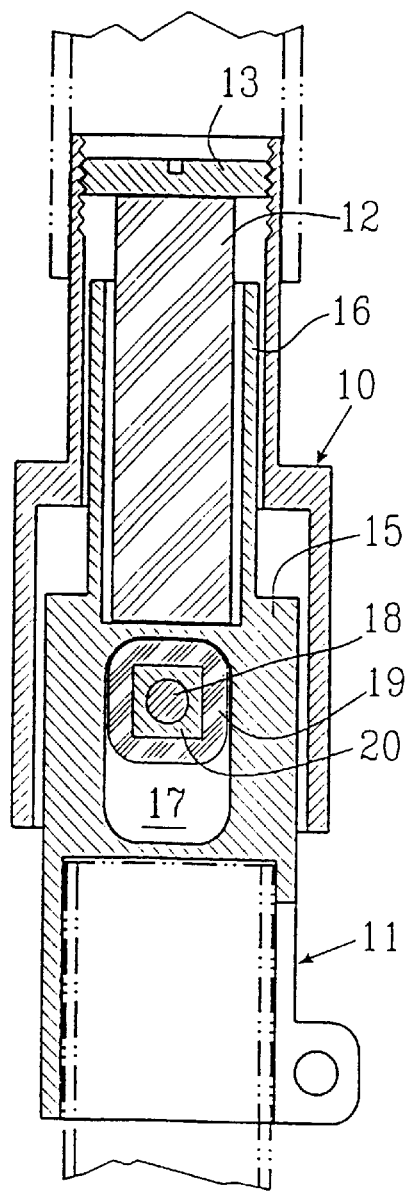

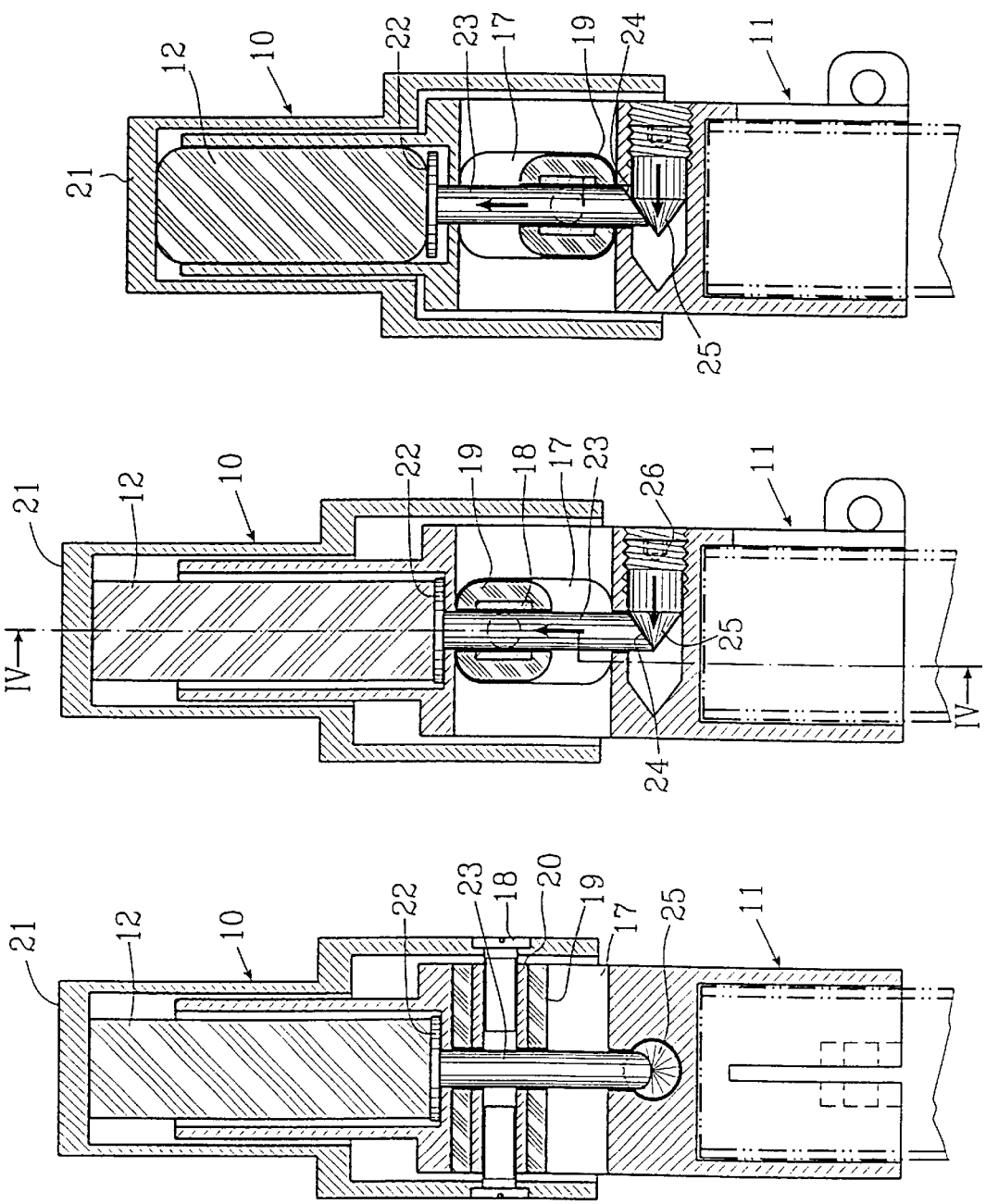

SHOCK-AND TORQUE ABSORBER IN A LEG PROTHESIS

TECHNICAL FIELD

The present invention refers to a device in a leg prosthesis provided with a shock- and torque absorber intended to absorb shocks as well as rotational movements which occur when the foot hits the ground during walking, running, jumping etc. and comprising two parts which are telescopically displaceable and rotatable with respect to each other and provided with damping means.

BACKGROUND OF THE INVENTION

A shock absorber in a leg prosthesis should be able to absorb linear as well as rotational forces which occur at heel strike when the foot hits the ground during activities such as walking, running, jumping etc. During walking and at heel strike the shock damping function of the artificial foot and sometimes also of the artificial knee is often unsufficient. However at such movements when the whole foot at the same time strikes the ground, e g when jumping and at quick movements such as running, there is needed a further shock absorption in order to avoid unpleasant shocks transferred to the part of the body to which the prosthesis is applied. Such shock absorbers which normally are placed in the lower leg part of the prosthesis often consist of hydraulic or pneumatic devices, which are relatively complicated and expensive.

In the leg prosthesis there is further needed a torque absorber which absorbs rotational movements in the artificial foot with respect to the leg prosthesis. One example of such a torque absorber is disclosed in U.S. Pat. No. 4,038,705.

OBJECT AND MOST IMPORTANT FEATURES OF THE INVENTION

The object of the present invention is to provide a device of the kind mentioned above, which can absorb shocks as well as torques and which has a simple and reliable construction. This has according to the invention been provided by means of a first resilient member arranged between the two telescopic parts and said resilient member is arranged to be compressed at a telescopic movement of said parts in a retracting direction, that a second resilient member is attached to the outer telescopic part and limitedly displaceable in the inner telescopic part limiting the telescopic movement as well as the rotational movement thereof in the outer telescopic part.

The shock absorber should further be simple to adjust in order to exert different counter pressures depending on the weight of the prosthesis wearer and the type of activity that is carried out, e g the counter pressure should be higher at running than at walking. This has been provided by the fact that the prestressing of the first resilient member is adjustable by means of adjustment means. Alternatively the first resilient member can be exchangeable and be of different hardness degrees. The same thing applies to the second resilient member.

Further features and advantages of the present invention are disclosed in the following description and the claims.

DESCRIPTION OF THE DRAWINGS

The invention will below be closer described with reference to a couple of embodiments shown in the accompanying drawings.

FIG. 1 is a vertical section through a first embodiment of the invention.

FIG. 2 is a section according the line II–II in FIG. 1.

FIG. 5 is a vertical section through a third embodiment of the invention.

FIG. 6 is a vertical section according to FIG. 5 but taken at an angle displaced 90° thereto.

FIG. 7 is a corresponding section as FIG. 6 but showing the device in a loaded position.

DESCRIPTION OF EMBODIMENTS

Figure 3:
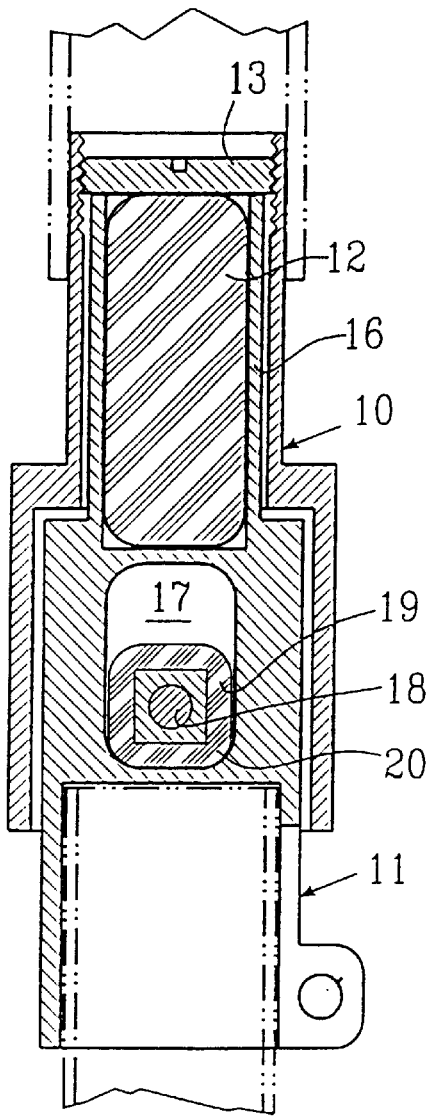
FIG. 3 is a corresponding section as FIG. 2 but showing the device in a loaded position.

In the drawings there is shown a leg prosthesis arranged either below or above the knee joint. The prosthesis comprises two telescopic parts 10 and 11 displaceable within each other and rotateable with respect to each other. A first resilient member 12 in the form of a block of rubber, polyurethane or similar material is clamped between the parts 10 and 11 and is arranged to be compressed when the parts 10 and 11 are displaced in a retracting direction.

According to the embodiment shown in FIGS. 1 and 2 the first resilient member 12 is clamped between a nut 13 screwed into the upper outer telescopic part 10 and a support surface 14 on a housing member 15 formed in the lower inner telescopic member 11. The resilient member 12 extends through a tubular portion 16 of the telescopic member 11, said portion has a somewhat larger cross sectional area than the resilient member 12 in the unloaded position thereof (FIGS. 1 and 2). By this a limited expansion of the resilient member 12 across the compression direction thereof is admitted when the telescopic parts 10 and 1l1 are pressed into each other (FIG. 3) upon an axial loading thereof. When the load is ceased the resilient member 12 returns to its initial position.

The nut 13 can be tightened against the resilient member 12 in different degrees in order to vary the counter pressure exerted when the telescopic parts 10, 11 are pressed into each other when the prosthesis is exerted to shocks. The counter pressure can need to be varied depending on the weight of the prosthesis wearer and the type of activity that is carried out, e g the counter pressure should be higher at running than at walking.

An alternative way to vary this counter pressure is simply to exchange the resilient member 12 for one of another elastic degree of hardness.

The housing member 15 of the telescopic part 11 is provided with a hollow space 17 extending across the housing member. The hollow space 17 has a larger extension in axial than in radial direction which can be seen from FIGS. 2 and 3. A bolt 18 extends through this hollow space 17, said bolt is attached to the outer telescopic part 10. A resilient sleeve 19 is arranged about the bolt 18, said sleeve constituting a second resilient member. A metal sleeve 20 having a square outer cross section can possibly be arranged between the resilient sleeve 19 and the bolt 20.

In the embodiment shown in FIG. 1 the hole for the bolt 18 in the wall of the outer telescopic member 10 is sufficiently large for the resilient sleeve 19 to be removed through said hole, e g in order to exchange it for another sleeve having a different degree of hardness.

The relative displacement of the telescopic parts 10 and 11 is limited by the axial length of the hollow space 17. In the maximum retracted position shown in FIG. 3 there should be a small allowance between all metal surfaces of the telescopic parts 10 and 11, such as between the nut 13 and the free end of the tubular part 16 and between the upper side of the housing portion 15 and the inside of the outer telescopic part 10. By this is is prevented that metal surfaces strike each other but the entire shock movement is instead absorbed by the resilient members 12 and 19. When the shock absorber is rapidly unloaded the element 12 presses the telescopic members 10 and 11 apart. This movement is softly braked without disturbing sounds by the resilient member 19 at the end position.

The second resilient member 19 has in unloaded position a very limited mobility in radial direction in the hollow space 17, which means that also rotational movements between the telescopic members 10 and 11 are elastically damped. At a torsional force right-left the resilient member 19 is compressed and admits depending on elastic stiffness and torsion force a rotation of between 0–30° with a gradually increasing resistance. When the force ceases the resilient member 19 returns to its initial position and forces thereby the telescopic parts 10 and 11 to return to its initial position. The second resilient member 19 can be exchangeable for another member having a different elastic degree of stiffness and by that vary the resistance exerted against rotational movements between the telescopic parts 10 and 11.

Figure 4:
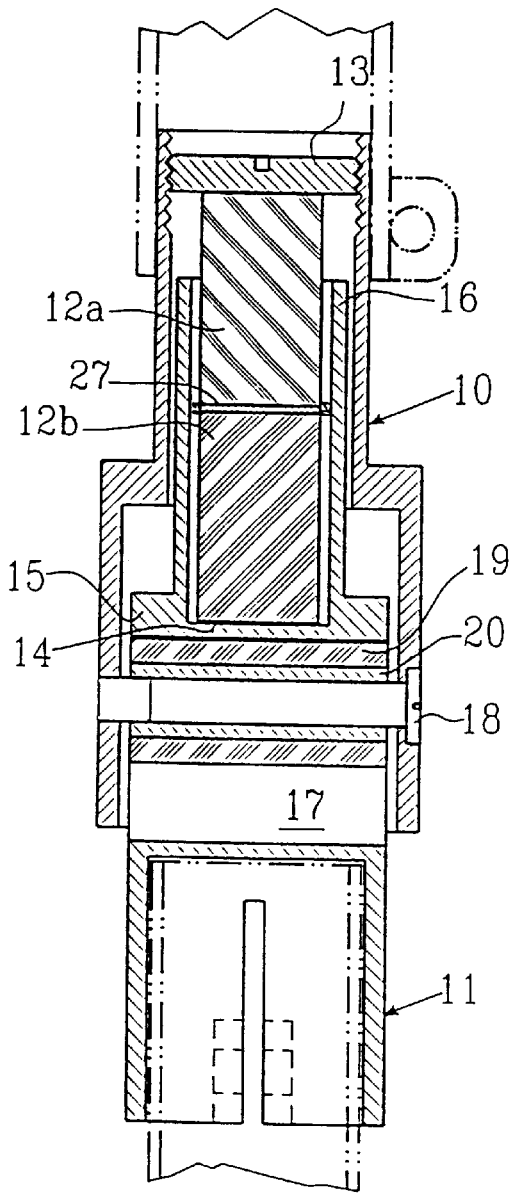
FIG. 4 is a vertical section through a second embodiment of the invention.

According to the embodiment shown in FIG. 4 the first resilient member 12 is divided in two portions, an upper 12a and a lower portion 12b, separated by a disc 27 of a hard material, e g metal or nylon. The two portions 12a and b are of different elastic degrees of stiffness, at which the upper portion 12a preferably is of a harder and the lower portion 12b of a softer material. By this a progressive damping with an increasing degree of loading is achieved. The lower softer portion 12b will be compressed first and expand in radial direction. The space in the tubular part 16 only admits a limited expansion of the lower part 12b for protecting this from being overcompressed. When the lower portion 12b has been compressed so much that is admitted by this limited space, a compression of the upper harder portion 12a is started at a further compression to the end position where the movement is caught and limited by the second resilient member 19.

The embodiment shown in FIGS. 5–7 differs from the one described above through the way of adjusting the first resilient member 12. While in the above described embodiment this adjustment only can be made when the prosthesis has been taken off, it is in the embodiment shown in FIGS. 4–6 possible to adjust the prestressing from the outside of the prosthesis also when this is on. The first resilient member 12 is in this case clamped between an end wall 21 of the outer telescopic part 10 and a plate 22 connected to a rod 23 which is axially displaceable in the inner telescopic part 11. The rod has a lower oblique surface 24, which cooperates with a corresponding oblique surface 25 of an adjustment screw 26 inserted in radial direction in the telescopic part 11. By tightening the adjustment screw 26 the rod 23 is pressed upwards at which the plate 22 is tightened against the first resilient member and increases the prestressing thereof.

Figure 8A:
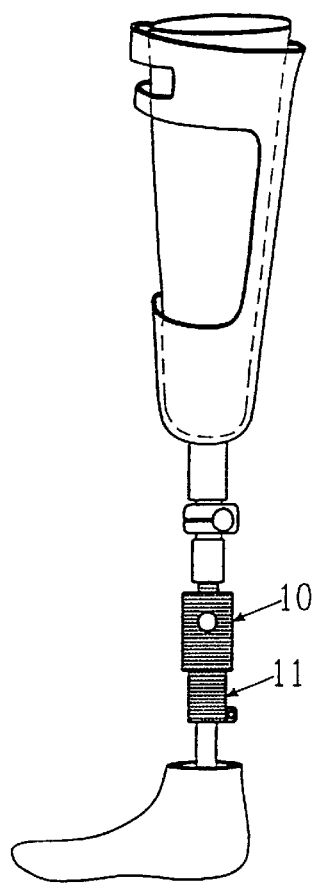
FIG. 8a–c show schematically different disposals of the device according to the invention in leg prostheses.
Figure 8B:
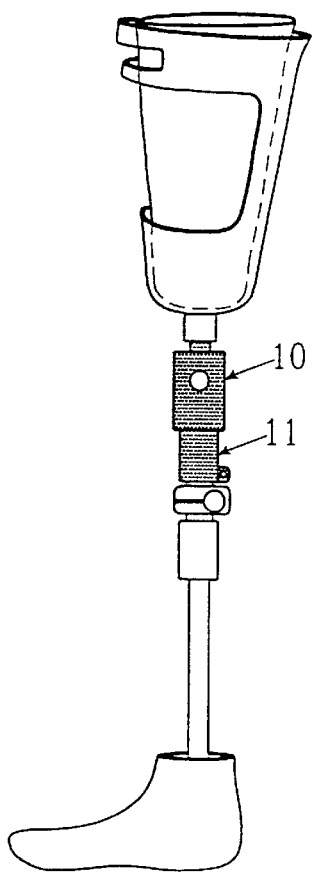
Figure 8C:
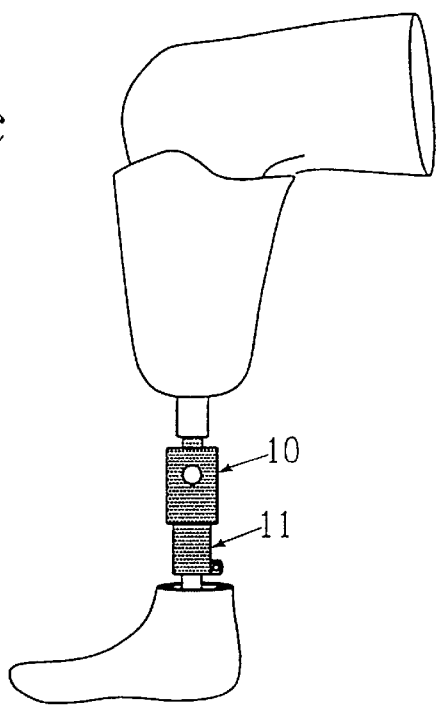

In FIGS. 8a–c it is shown how the leg prosthesis part according to the invention can be placed in different types of leg prostheses. In FIG. 8a is shown how it can be mounted in an upper leg prosthesis below the mechanic knee joint. In FIG. 8b it is mounted in an upper leg prosthesis above the mechanic knee joint and in FIG. 8c it is mounted in a lower leg prosthesis.

The leg prosthesis part consisting of the two telescopic parts 10 and 11 are at first hand intended to be mounted below the knee joint, which either is a mechanical or a natural knee joint, as is shown in FIGS. 8b and c. The resilient members 12 and 19 can by this absorb shocks as well as torsional forces which occur at heel strike when walking, running, jumping etc. The two resilient members 12 and 19 keep in unloaded position the two telescopic parts 10 and 11 in a fixed position. The resilient members also act as energy accumulators as the energy stored in them at the compression is returned at toe off when the foot leaves the ground, at which the shock absorbers expand to their initial position. The energy consumption when walking or running is by this minimized.

A further advantage with the shock- and torque absorber according to the invention is that one obtains an automatic tilting compensation when the prosthesis is unevenly loaded. A problem always occurring in short telescopic elements is that they due to the short support bearing have a tendency to seize when the inner telescopic part is heavily loaded from the side and tilts in its bearings. Such a tendency to seizing is very. unpleasant in a leg prosthesis and gives a hard and jerky movement up and down. The critical moment is when the shock absorber is compressed and in a position with the loading on the toe section. The prosthesis wearer is in a position to unload the shock absorber by lifting the foot from the floor. Due to the lateral force in the loading there is a risk for seizing between the telescopic parts. At unloading the telescopic parts can be pushed apart with a sudden jerk when the lateral force is reduced and the resilient damping element momentaneously can overcome the friction in the seizing position.

Figure 9:
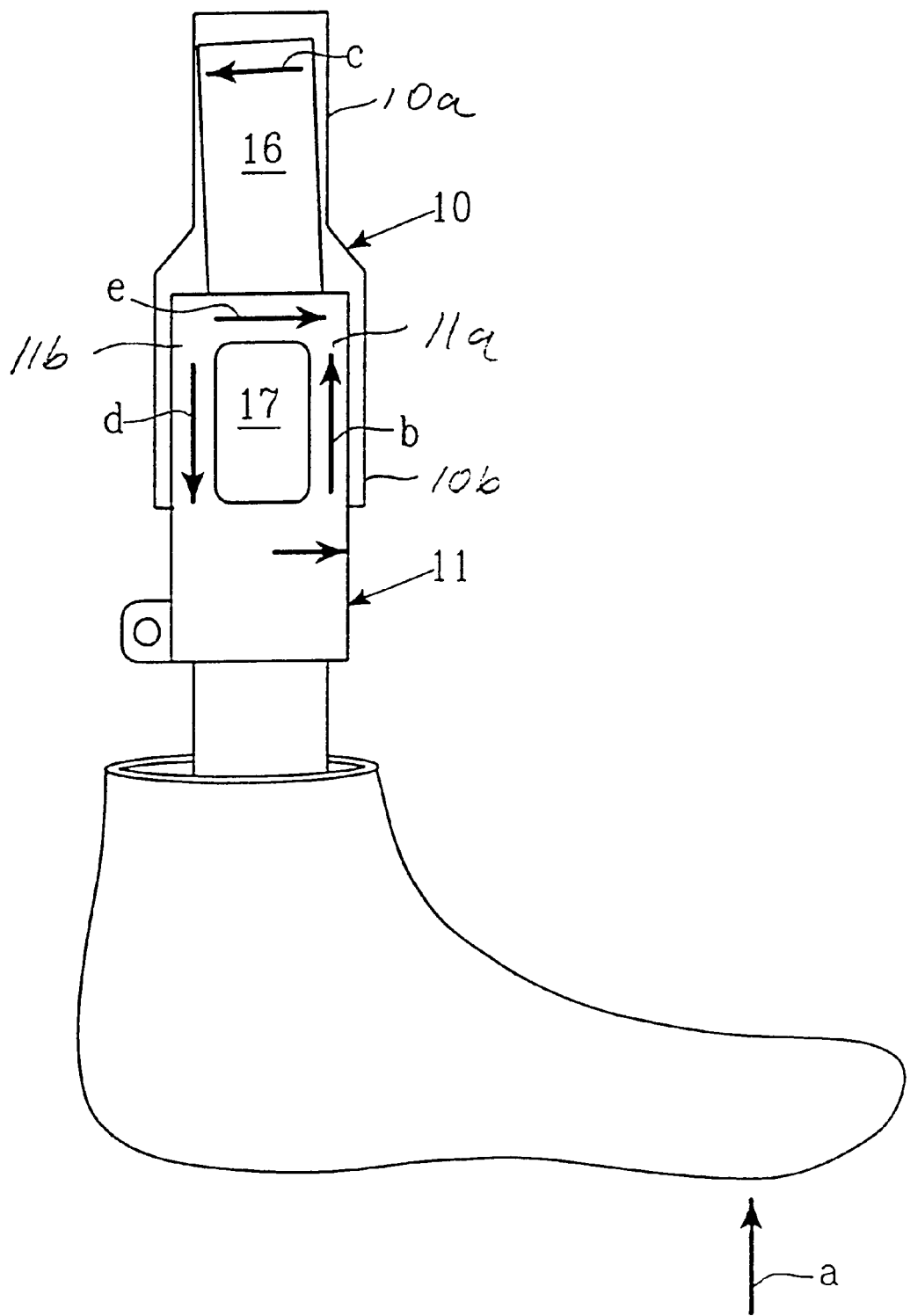
FIG. 9 illustrates schematically how a mechanic counter movement is created in the device which prevents obliqueness at an uneven load.

In the damper according to the invention there is provided an automatic mechanical counter movement which counteracts such an obliquity and which creates a force which all the time strives for maintaining the largest bearing surfaces of the inner telescopic member 11 in parallel. This is illustrated in FIG. 9. The hollow space 17 contributes to that the inner telescopic part 11 forms a flexible unit having two leg portions 11a, 11b on either side of the hollow space 17, which due to a certain resiliency in the material can be somewhat displaced with respect to each other at an uneven load.

The force at the arrow a passes up through the inner telescopic part 11 and pushes the leg 11a upwards according to the arrow b. The second leg 11b is forced downwards according to the leg d. This displacement causes the part 16 to slightly tilt according to the arrow c. This tilting movement is counteracted by the small bearing 10a for the part 16 and forces the inner telescopic part 11 to straighten the obliquity in the big bearing 10b in the outer telescopic movement 10. By the fact that the bearing surfaces in the big bearing 10b are forced to a higher degree of parallellism the friction is noticably reduced. The friction is somewhat increased in the small bearing 10a, but due to the considerably smaller diameter therein and by this a longer bearing surface with respect to diameter, this bearing is less sensitive to tiling. The total contact surface is also smaller and gives a considerably lower friction than the big bearing. 10b. Another important friction reducing function is also that the thin-walled big bearing 10b of the upper telescopic member 10 during lateral loading will circularly shape itself after the inner telescopic part 11 and by this distributes the loading better and reduces the risk for a high surface pressure on the bearing.

The invention is of course not limited to the embodiments shown in the drawings but can be modified within the scope of the claims.

What is claimed is:

1. A device on a leg prosthesis provided with a shock and torque absorber intended to absorb shocks as well as rotational movements which occur when the foot hits the ground during walking, running, and jumping and comprising two parts, an outer telescopic part and an inner telescopic, which are telescopically displaceable and rotatable with respect to each other and provided with damping means, and wherein a first resilient member is arranged between the two telescopic parts and said resilient member is arranged to be compressed at a telescopic movement of said parts in a retracting direction, characterized in that a second resilient member is arranged about an axle which is attached to the outer telescopic part, the axle extending through a hollow space therein, said hollow space having a limited extension in axial as well as radial direction, so that the second resilient member is limitedly displaceable in the inner telescopic part and softly and flexibly limiting the telescopic movement as well as the rotational movement thereof in the outer telescopic part.

2. A device according to claim 1, characterized in that a pre-stressing of the first resilient member is adjustable by adjustment means.

3. A device according to claim 1, characterized in that the first and/or second resilient member are exchangeable from the outside and without the need for dismounting the telescopic parts and are provided in different elastic degrees of hardness.

4. A device according to claim 1, characterized in that the first resilient member is received in a tubular part in one of the telescopic parts, said tubular part admitting a limited expansion of the first resilient member across the compression direction thereof.

5. A device according to claim 1, characterized in that the first resilient member is divided in an upper and lower portion of different elastic degrees of hardness and separated by a disc or the like of hard material for providing a progressive damping.

6. A device according to claim 5, characterized in that the lower portion is of a softer and more easily compressible material than the upper portion, and that the space for expansion of the lower softer portion is limited in order to protect the lower portion from over compression and instead cause the upper harder portion to be compressed at an additional loading when a further expansion of the lower portion is prevented.

7. A device according to claim 1, characterized in that the second resilient member is compressed at a rotational movement between the telescopic parts and admits depending on elastic hardness and torsional force a limited rotation with a gradually increasing resistance.

8. A device according to claim 1, characterized in that the limited mobility of the second resilient member in the hollow space in axial and radial direction elastically limits the displacement of the inner telescopic part in axial direction as well as its rotational movement in the outer telescopic part.

9. A device according to claim 1, characterized in that the inner telescopic part is provided with two substantially parallel leg portions separated by the hollow space and having a certain flexibility and ability to be displaced with respect to each other and force the tubular part to straighten up the rest of the inner telescopic part and by this prevent obliquity of the telescopic parts at an uneven loading of the device.

10. A device according to claim 1, characterized in that the first and second resilient members in unloaded positions keep the two telescopic parts in a fixed position.

* * * * *